United States Patent [19]

Kwiatkowski et al.

[11] Patent Number: 5,777,168

[45] Date of Patent: Jul. 7, 1998

[54] PROCESS FOR PRODUCING N-ALKYL-DINITROALKYLANILINES

[75] Inventors: Stefan Kwiatkowski; Krzysztof Pupek; Brenda L. Lawrence; Lowell J. Lawrence, all of Richmond, Ky.

[73] Assignee: SRM Chemical, Ltd. Co., League City, Tex.

[21] Appl. No.: 868,321

[22] Filed: Jun. 3, 1997

Related U.S. Application Data

[63] Continuation-in-part of Ser. No. 496,774, Jun. 29, 1995, Pat. No. 5,689,006.

[51] Int. Cl.$^6$ .................................................. C07C 209/18
[52] U.S. Cl. ............................................. 564/399; 564/87
[58] Field of Search ....................................... 564/399, 87

[56] References Cited

U.S. PATENT DOCUMENTS

| | | |
|---|---|---|
| 3,672,866 | 6/1972 | Damiano . |
| 3,927,127 | 12/1975 | Damiano . |
| 3,991,116 | 11/1976 | Damiano . |
| 4,289,907 | 9/1981 | Chan . |
| 4,395,572 | 7/1983 | Chan . |

FOREIGN PATENT DOCUMENTS 0 630 883   12/1994   European Pat. Off. .

OTHER PUBLICATIONS

Olson, Walter T. et al.; "The Synthesis and Purification of Ethers"; Journal of the American Chemical Society; vol. 69, No. 10; Oct. 31, 1947; 2451–4.

Dubinin, B.M.; "Isomerizations in Organomagnesium Synthesis" Chemical Abstracts; vol. 44, No. 3; Feb. 10, 1950; 1060.

*Primary Examiner*—Brian M. Burn
*Attorney, Agent, or Firm*—King and Schickli

[57] ABSTRACT

This invention relates to a process for producing N-alkyl-dinitroalkylaniline and particularly N-sec-butyl-4-tert-butyl-2,6-dinitroaniline by methylation of an alkylphenol followed by a one or two stage dinitration of the resulting alkylanisole which is followed by reaction with an amine.

11 Claims, No Drawings

5,777,168

1

PROCESS FOR PRODUCING N-ALKYL-DINITROALKYLANILINES

This is a continuation-in-part of U.S. patent application Ser. No. 08/496,774, filed on Jun. 29, 1995 and entitled "Process for Producing N-Alkyl-Dinitroalkylanilines" (now U.S. Pat. No. 5,689,006).

TECHNICAL FIELD

The present invention relates generally to an improved process for the production of N-alkyl-dinitroalkylanilines in a more cost effective and efficient manner.

BACKGROUND OF THE INVENTION

N-alkyl-dinitroalkylanilines such as N-sec-butyl-4-tert-butyl-2,6-dinitroaniline |(1,1-dimethylethyl)-N-|1-methylpropyl)-2,6,dinitrobenzenamine; butralin| are known selective herbicides generally used for pre-emergence control of annual broad-leaved weeds and grasses in cotton, soybeans, rice, barley, beans, alliums, vines, ornamentals and orchards of fruit and nut trees. They are also used to control suckers of tobacco.

The synthesis of N-sec-butyl-4-tert-butyl-2,6-dinitroaniline is generally described in a number of U.S. patents including, for example, U.S. Pat. Nos. 3,672,866; 3,927,127 and 3,991,116 all to Damiano. The process described in U.S. Pat. Nos. 3,672,866 and 3,991,116 begins with a starting material, 4-tert-butylphenol. The 4-tert-butylphenol is subjected to nitration utilizing nitric acid in acetic acid solution to produce 2,6-dinitro-4-tert-butylphenol. The 2,6-dinitro-4-tert-butylphenol is then chlorinated to produce 2,6-dinitro-4-tert-butylchlorobenzene. This 2,6-dinitro-4-tert-butylchlorobenzene is then converted into N-sec-butyl-4-tert-butyl-2,6-dinitroaniline by amination with sec-butylamine.

While this process is effective in producing the desired product, it does suffer from a number of distinct disadvantages. First and foremost is the relatively low yield of the nitration step: only approximately 70%. Second, the process necessitates purification of the 2,6-dinitro-4-tert-butylphenol product of the nitration step by crystallization from large volumes of highly volatile and flammable hexane. This is both hazardous and time consuming. Third, is the necessity of utilizing thionyl chloride in high boiling and expensive solvents for the chlorination step. This step disadvantageously leads to the equimolar formation of toxic and environmentally hazardous gaseous by-products; hydrochloric acid and sulfur dioxide. Further, the slow fifteen hour process also necessitates further purification of the crude product from hexane thereby further elevating the costs of production. Fourth, the amination step requires seven hours and the use of excessive amounts of sec-butylamine while unfortunately being accompanied by the formation of equimolar quantities of sec-butylamine hydrochloride as a by-product.

The process described in U.S. Pat. No. 3,927,127 begins with a starting material, 4-tert-butylchlorobenzene. The 4-tert-butylchlorobenzene is subjected to nitration utilizing a mixture of nitric and sulfuric acids to produce 2,6-dinitro-4-tert-butylchlorobenzene. The 2,6-dinitro-4-tert-butylchlorobenzene is then converted to N-sec-butyl-4-tert-butyl-2,6-dinitroaniline by amination with sec-butylamine. While the process is effective in producing the desired product, it does suffer from a number of distinct shortcomings. First and foremost, it is necessary to use a highly concentrated nitric and sulfuric acid mixture at elevated temperatures for a prolonged time to complete the nitration step of the synthesis. This unfortunately involves a substantial risk of explosion. Second, it is necessary to use an excess of sec-butylamine because of the equimolar formation of a sec-butylamine hydrochloride as a by-product in the third stage of the process. This, unfortunately, necessitates the application of a high boiling point solvent (e.g. xylene) to allow filtration separation of the by-product thereby producing a number of additional safety hazards and environmental concerns.

An alternative synthesis for N-sec-butyl-4-tert-butyl-2,6-dinitroaniline is set forth in U.S. Pat. Nos. 4,289,907 and 4,395,572 to Chan. The starting material in this synthesis is a nitrophenol such as 2,6-dinitro-4-tert-butylphenol. The nitrophenol is methylated by reaction with methyl iodide/potassium carbonate to produce 4-tert-butyl-2,6-dinitroanisole. The 4-tert-butyl-2,6-dinitroanisole is then reacted with sec-butylamine to produce N-sec-butyl-4-tert-butyl-2,6-dinitroaniline. While effective in producing the desired product, this process also suffers from a number of distinct disadvantages.

First, the process involves the use of methyl iodide. This material is expensive, volatile, carcinogenic and poisonous. The resulting health and environmental concerns require the establishment of special handling procedures.

Second, the resulting yield of the process is only approximately 71%. Third, the product is accompanied by the formation of bulk amounts of gaseous, liquid and solid waste including the carcinogenic methyl iodide starting material. Fourth, the process involves the use of excess amounts of potassium carbonate and highly flammable and volatile acetone as a solvent. This adds to the expenses and handling concerns of the process.

From the above description it should be appreciated that a need exists for an improved process for producing N-alkyl-dinitroalkylanilines in a more economical and environmentally safer manner.

SUMMARY OF THE INVENTION

Accordingly, it is a primary object of the present invention to provide a process for the production of N-alkyl-dinitroalkylanilines including, for example, N-sec-butyl-4-tert-butyl-2,6-dinitroaniline overcoming the above-identified limitations and disadvantages of the prior art.

Another object of the invention is to provide a process for the production of N-alkyl-dinitroalkylaniline from readily available and relatively inexpensive starting materials and relatively safe and inexpensive reagents whereby the environmentally safe and economical production of N-alkyl-dinitroalkylaniline results.

Other objects and advantages of the present invention will become apparent as the description hereof proceeds.

In satisfaction of the foregoing objects and advantages there is provided by this invention a process for producing N-alkyl-dinitroalkylanilines. The process generally comprises the reacting of an alkylphenol with a methylating agent such as dialkyl sulfate to produce an alkylanisole intermediate. The alkylanisole intermediate is then reacted with a nitrating agent such as nitric acid, a mixture of nitric and sulfuric acid or nitrogen dioxide to produce a dinitro-substituted alkylanisole. The dinitro-substituted alkylanisole is then reacted with an amine to produce the desired N-alkyl-dinitroalkylaniline product.

More specifically, the process for producing N-sec-butyl-4-tert-butyl-2,6-dinitroaniline comprises reacting 4-tertbutylphenol with dimethyl sulfate to produce 4-tert-butylanisole. The 4-tert-butylanisole is then reacted with a nitrating agent including a mixture of nitric acid, sulfuric acid and oleum to produce 2,6-dinitro-4-tert-butylanisole. The 2,6-dinitro-4-tert-butylanisole is then reacted with sec-butylamine to produce N-sec-butyl-4-tert-butyl-2,6-dinitroaniline.

DETAILED DESCRIPTION OF THE INVENTION

As indicated above, the present invention relates to a process for producing N-alkyl-dinitroalkylanilines of a type known to be useful as selective herbicides used for pre-emergence control of annual broad-leaved weeds and grasses in, for example, cotton, soybeans, rice, barley, beans, alliums, vines, ornamentals and orchards of fruit and nut trees as well as to control suckers of tobacco.

The process may be generally described as comprising the steps of: (1) reacting an alkylphenol with a methylating agent to produce an alkylanisole intermediate; (2) reacting the alkyl anisole intermediate with a nitrating agent including a mixture of nitric acid, sulfuric acid and oleum to produce a dinitro-substituted alkylanisole; and (3) reacting the dinitro-substituted alkylanisole with an amine to produce N-alkyl-dinitroalkylaniline.

More specifically describing the invention, the first step of the synthesis includes the preparing of an aqueous suspension of alkylphenol followed by the adding of sodium hydroxide and a dialkyl sulfate such as dimethyl sulfate into the aqueous suspension at a temperature of between substantially 5°–55° C. while maintaining a pH between substantially pH 7.5–9.5. This is followed by the collecting of the alkylanisole intermediate which is formed as an upper layer on the two layer system that is produced.

The second or nitration step of the synthesis may be performed in accordance with either of two different approaches. The first approach is a two stage nitration. Specifically, the alkylanisole intermediate from the first step of the process is mononitrated in an organic solvent such as ethylenedichloride using 70% concentrated nitric acid. The reaction is exothermic and fast but is relatively easy to control by adjusting the rate of nitric acid addition and the temperature of the cooling medium. Preferably the reaction is maintained at a temperature below 10° C. and is completed in only a few hours yielding a mixture of mononitro-substituted alkylanisole and a mononitroanisole byproduct in a molar ratio of about 72.5:27.5.

The desired mononitro-substituted alkylanisole is separated from the mononitroanisole byproduct by means of vacuum distillation. The mononitro-substituted alkylanisole intermediate is then subjected to the second stage of nitration. Specifically, the mononitro-substituted alkylanisole intermediate is nitrated in an organic solvent such as ethylenedichloride using 70% or more concentrated nitric acid in a mixture with 98% sulfuric acid. The reaction is exothermic and requires cooling with an ice-water bath to maintain a temperature at or below 10° C. during the time of addition of the nitration mixture and then heating to maintain a temperature of approximately 50° C. to complete the conversion of the mononitro-substituted alkylanisole to the desired nitro-substituted alkylanisole. Similar to the mononitration stage, the second stage of nitration produces a dinitro-substituted anisole byproduct. The molar ratio of the desired dinitro-substituted alkylanisole to the dinitro-substituted anisole by-product formed is approximately 10:1. A small amount (below approximately 2%) of the mononitro-substituted alkylanisole is also present in the post reaction mixture even after extended reaction time. The solvent is utilized in this dinitration stage in order to avoid or limit the formation of trinitro-substituted anisole byproduct.

The desired dinitro-substituted alkylanisole is now separated from the dinitro-substituted anisole byproduct. Specifically, the stirring and heating of the reaction mixture is stopped. The mixture then separates into an upper organic layer and a lower waste acid layer. The upper organic layer is collected and without additional purification is subjected to evaporation of the ethylene dichloride solvent in a rotary evaporator under 20 mmHg at 40° C. Next, the reaction products are subjected to hydrolytic separation. The reaction products are first diluted with water and the pH of the water layer is then adjusted to 7.5 by the addition of a hydroxide such as sodium hydroxide. The mixture is then boiled for at least an hour. Next, the mixture is cooled and extracted with ethylene dichloride. The extract is then concentrated by evaporation of the ethylene dichloride in a rotary evaporator. The resulting product is then crystallized from methanol to yield the desired dinitro-substituted alkylanisole intermediate.

An alternate approach to that described above is a single stage dinitration. In this approach there is no intermediate separation of the mononitro-substituted alkylanisole intermediate from the mononitro-substituted anisole byproduct. Specifically, the alkylanisole intermediate from the first step of the process is mononitrated at first in an organic solvent such as ethylene dichloride using one equivalent of approximately 98% concentrated nitric acid. The reaction is exothermic and the reaction mixture is preferably maintained below approximately 5° C. during the addition. The temperature of the reaction mixture is then allowed to rise to approximately 20° C. to complete the reaction. After this time, the temperature of the reaction mixture was decreased to 0° C. by cooling in an ice-water bath and a mixture of concentrated nitric acid, concentrated sulfuric acid and oleum was dropped while maintaining efficient stirring and cooling, at such a rate as to maintain the temperature of the reaction below 5° C. After completion of the addition the temperature of the reaction mixture was increased to 40° C within 2 hours and maintained for an additional 3 hours Then the organic (upper) layer was separated and the solvent removed from it by means of rotary evaporation at 40° C under 20 mmHg to yield a mixture of the desired dinitro-substituted alkylanisole and a dinitro-substituted anisole byproduct in a ratio of approximately 64:34. The desired dinitro-substituted alkylanisole intermediate is separated from the dinitro-substituted anisole byproduct by means of hydrolytic separation in the manner previously described using a hydroxide such as sodium hydroxide.

The third step of the synthesis may be more specifically described as including the mixing of substantially two part by weight dinitro-substituted alkylanisole intermediate with substantially one part of amine (e.g. sec-butylamine) at a temperature of above substantially 45° C. for at least on hour. This is followed by diluting the reaction mixture with one volume part of methanol and filtration of the product Stated another way, the process may be broadly describe as including the steps of reacting an alkylphenol with methylating agent selected from a group consisting o dialkylsulfates to produce a first reaction intermediate. Thi first reaction may be described as follows:

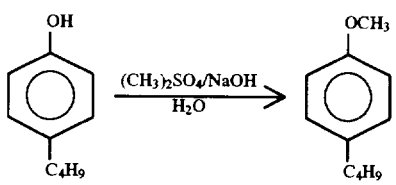

Next is the reacting of the first reaction intermediate with a nitrating agent selected from but not limited to a group consisting of nitric acid, a mixture of nitric acid and sulfuric acid and a mixture of nitric acid, sulfuric acid and oleum to produce a second reaction intermediate.

This second reaction may be described as follows:

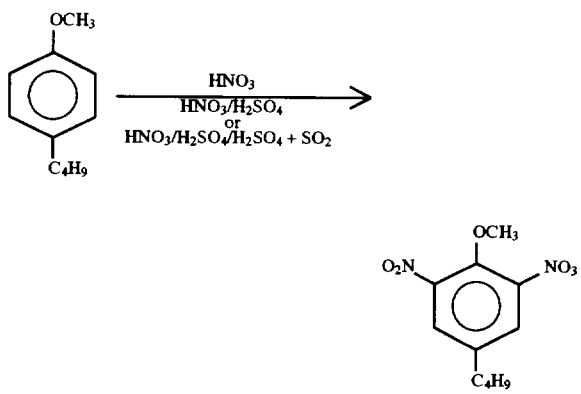

This is followed by the reacting of the second reaction intermediate with an amine selected from a group including sec-butylamine and 1-ethylpropylamine to produce N-alkyl-dinitroalkyl-anilines. This third reaction may be described as follows:

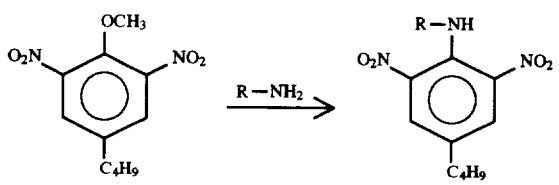

wherein R=sec-butyl-, 1-ethylpropyl-.

The detailed procedural description of these broadly described reaction steps is exactly as previously described.

The process of the present invention for producing N-alkyl-dinitroalkylanilines may also utilize alkylanisole starting material. In this situation it is a two step procedure: that is the reacting of an alkylanisole with a nitrating agent selected from a group consisting of nitric acid, a mixture of nitric acid and sulfuric acid and a mixture of nitric acid, sulfuric acid and oleum to produce a reaction intermediate and the reacting of the reaction intermediate with an amine selected from a group consisting of sec-butylamine and 1-ethylpropylamine, to produce the N-alkyl-dinitroalkylaniline.

In accordance with a more specific aspect of the present invention, a process is provided for producing N-sec-butyl-4-tert-butyl-2,6-dinitroaniline. The process may be broadly described as: (1) reacting 4-tert-butylphenol with dimethyl sulfate to produce 4-tert-butylanisole (a methylation reaction); (2) reacting the 4-tert-butylanisole with nitric acid, a reacting the 4-tert-butylanisole with nitric acid, a mixture of nitric acid and sulfuric acid or a mixture of nitric acid, sulfuric acid and oleum to produce 2,6-dinitro-4-tert-butylanisole (a nitration reaction); and (3) reacting the 2,6-dinitro-4-tert-butylanisole with sec-butylamine to produce N-sec-butyl-4-tert-butyl-2,6-dinitroaniline (an amination reaction).

More specifically describing the process, initially there is the preparing of an aqueous suspension of 4-tert-butylphenol. This is followed by the adding of sodium hydroxide and dimethyl sulfate into the aqueous suspension at a temperature of between substantially 5°–55° C. while maintaining a pH between substantially pH 7.5–9.5. This is followed by the collecting of the 4-tert-butylanisole as an upper layer of the two layer system that is produced. The 4-tert-butylanisole may be purified, if desired, by any manner known in the art including distillation.

Next is the mixing of one part 4-tert-butylanisole with between substantially 0–9 parts (by volume) organic solvent such as ethylene dichloride. Next is the cooling of the reaction mixture of 4-tert-butylamine and organic solvent to a temperature below 5° C. This is followed by the adding of 70% concentrated nitric acid while maintaining the temperature of the reaction mixture below 10° C. to produce 2-nitro-4-tertbutylanisole and a 4-nitroanisole byproduct. These are separated by means of vacuum distillation. Specifically, the 4-nitroanisole byproduct has a boiling point of 86° C. while the desired 2-nitro-4-tertbutylanisole has a boiling point of 102°–105° C. at a pressure of 1 mmHg.

The recovered 2-nitro-4-tertbutylanisole is then again subjected to nitration. Specifically, the 2-nitro-4-tertbutylanisole intermediate is mixed with between 2–9 parts (by volume) organic solvent such as ethylene dichloride. Next is the cooling of the reaction mixture of 2-nitro-4-tertbutylanisole and organic solvent in an ice-water bath to a temperature below 5° C. This is followed by the adding of a mixture of 70% nitric acid and 98% sulfuric acid while maintaining a temperature below 10° C. Following the acid mixture addition, the cooling bath is removed and the temperature of the reaction mixture is increased to 50° C. and maintained there for 2–10 hours to produce 2,6-dinitro-4-tertbutylanisole and a 2,4-dinitrophenol byproduct.

Alternatively, the dinitration just described may be complete in a single stage without the intermediate step of separating the 2-nitro-4-terbutylanisole from the 4-nitroaniline byproduct. This is accomplished by the mixing of one part 4-tert-butylanisole with between substantially 2–9 parts (by volume) organic solvent such as ethylene dichloride. This reaction mixture is then cooled in an ice-water bath to a temperature below 5° C. This is followed by the adding of a mixture of pure 98% nitric acid under stirring while maintaining the temperature below 5° C. Following this addition, the cooling bath is removed and the reaction mixture is heated and maintained at 20° C. for ½–3 hours to complete the reaction.

Next, the reaction mixture is cooled in an ice-water bath to 0° C. and an acid mixture of 98% nitric acid, 98% sulfuric acid and oleum is added with stirring while maintaining a temperature below 5° C. The temperature of the reaction mixture is then gradually increased over a two hour period to 40° C. and maintained at that temperature for another 3 hours to complete the reaction and produce 2,6-dinitro-4-tertbutylanisole and a 2,4-dinitrophenol byproduct.

Following completion of either the two stage or single stage dinitration just described, the desired 2,6-dinitro-4-tertbutylanisole intermediate is separated from the 2,4-dinitrophenol and other byproducts. Specifically, the heating and stirring are stopped and the reaction mixture separates into an upper organic layer and a lower waste acid layer. These layers are separated and the acid layer is washed with ethylene dichloride or other appropriate organic solvent in order to recover any residual desired reaction product from that layer. The ethylene dichloride wash solution is then added to the organic layer which is subjected to concentration by means of a rotary evaporator operating at 40° C. under 20 mmHg. This drives off the ethylene dichloride which may be collected and recycled for use in the next batch process.

The concentrated reaction products are then subjected to hydrolytic separation. Specifically, the concentrated reaction products are first diluted with water and then the pH of the water layer is adjusted to 7.5 by the addition of e.g. sodium hydroxide. The mixture is boiled for at least an hour, then cooled and extracted with ethylene dichloride. The 2,6-dinitro-4-tertbutylanisole extract is then concentrated by evaporation of the ethylene dichloride solvent in a rotary evaporator. The resulting 2,6-dinitro-4-tert-butylanisole may be purified, if desired, by washing with cold methyl alcohol.

Two parts of the recovered 2,6-dinitro-4-tert-butylanisole is then mixed with substantially one part sec-butylamine at a temperature of above substantially 45° C. for at least one hour and more preferably four hours. This is followed by the diluting of the reaction mixture with one volume part of methyl alcohol and filtration to collect the N-sec-butyl-4-tert-butyl-2,6-dinitroaniline product.

In accordance with another aspect of the present invention, a two step process for producing N-sec-butyl-4-tert-butyl-2,6-dinitroaniline comprises the steps of reacting 4-tert-butylanisole with a nitrating agent selected from a group consisting of nitric acid, a mixture of nitric acid and sulfuric acid and a mixture of nitric acid, sulfuric acid and oleum to produce a reaction intermediate and reacting the reaction intermediate with sec-butylamine to produce N-sec-butyl-4-tert-butyl-2,6-dinitroaniline.

Advantageously, the process of the present invention produces high yields of the product being a minimum of 97% pure if high purity reagents are utilized. The following synthesis and examples are presented to further illustrate the invention, but it is not to be considered as limited thereto.

EXAMPLE 1

A solution of 8.2 g (50 mmole) of 4-tertbutylanisole in 15 ml of ethylene dichloride was placed in a 40 ml two necked round-bottomed flask equipped with a thermometer, a dropping funnel and magnetic stirring bar. The flask was placed in an ice-water bath and the contents were stirred and cooled. When the temperature reached +4° C., 4.72 g (3.32 ml, 52.4 mmol) of 70% nitric acid was added at such a rate that the temperature of the reaction mixture remained below 10° C. The completion of the acid addition took 15 minutes. Then the reaction mixture was stirred for 15 minutes while the flask was still immersed in the ice-water bath. After this time the reaction mixture was allowed to warm-up to 23° C. and left for 3 more hours with stirring to complete the nitration. The stirring was then stopped and the lower (organic) layer was collected. From this solution ethylene dichloride is removed by rotary evaporation at 40° C. under 20 mmHg and an oily residue was subjected to vacuum distillation. A 6" Vigreux column and a pressure of 1 mmHg was applied. These conditions afforded separation of the 4-nitroanisole bp 86° C. from 2-nitro-4-tertbutylanisole bp 102°–105° C. It resulted in the collection of 7.576 g of 99.1% pure 2-nitro-4-tertbutylanisole and 2.116 g of 96.4% pure 4-nitroanisole, mp 54° C. wth a total yield of 72.5% of 2-nitro-4-tertbutylanisole.

Identical results were obtained in mononitrations in which (a) 50% nitric acid was used, at the reaction temperature of 80° C. and (b) 98% nitric acid was used, at the reaction temperature of –15° C.

EXAMPLE 2

Into a solution of 4-tert-butylanisole 1.6 g (9.7 mmol) in glacial acetic acid (5 mL), 0.7 ml (14.9 mmol, 1.5 eq.) of 90% nitric acid was added dropwise at room temperature with good stirring. The temperature and stirring were maintained for additional 3 hours. Next, the reaction mixture was poured into water/ice mixture of approximately 30 mL, and the resulting mixture was extracted with dichloromethane (2×10 mL). The combined organic extracts were then dried over anhydrous sodium sulfate. The dichloromethane solution was concentrated in a rotary evaporator at 40° C. temperature and 20 mmHg pressure to yield 1.72 g of liquid residue. The NMR analysis showed that the ratio of 4-tertbutyl-2-nitroanisole to 4-nitroanisole, in the residue, was 73:27. The same ratio of both products was obtained for the reaction carried out with 70% nitric acid at the temperature of 70° C.

EXAMPLE 3

Through a stirred and cooled to –15° C. solution of 4-tert-butylanisole 1.6 g (9.7 mmol) in ethylene dichloride (10 mL) a stream of gaseous nitrogen dioxide was slowly bubbled. The reaction mixture became deep green. This indicated the formation of $NO_2$-anisole complex. Next, the reaction mixture was slowly allowed to reach room temperature, while $NO_2$ was still bubbled. After 2 hours the color of the solution turned to yellow-brown and the reaction was completed (no starting material was detected by TLC). To separate the products, the reaction mixture was diluted with dichloroethane (15 mL) and successively washed with: water (25 mL), saturated water solution of sodium carbonate (25 mL) and water (25 mL). The organic phase was dried over anhydrous $Na_2SO_4$, and the solvent was removed in a rotary evaporator operating at 40° C. temperature and 20 mmHg pressure. Yield of the crude residue was 1.87 g. The ratio of 2-nitro-4-tert-butylanisole to 4-nitroanisole, in the residue, was determined by NMR to be 71:29.

EXAMPLE 4

A mixture of water (3.0 mL), nitric acid (70% 4.2 mL) and sulfuric acid (98%, 2.6 mL) was heated to 35° C. and then a solution of 4-tert-butylanisole (3.0 g, 183. mmol) in dichloromethane (5 mL) was dropped to the stirred mixture of acids within 1 hour. During the time of addition, the reaction mixture was vigorously stirred. Next, the reaction mixture was cooled to room temperature and diluted with dichloromethane (15 mL). The water layer was separated and the organic layer was washed with 5% sodium hydroxide (10 mL), followed by washing with 25 ml of water. After drying with anhydrous sodium sulfate the solution was filtered and concentrated by means of rotary evaporation a 40° C. temperature and 20 mmHg pressure to yield 1.62 g o oily residue. The ratio of 2-nitro-4-tert-butylanisole to 4-nitroanisole in this mixture determined by means of NMF to be 72:28.

The desired product of the mononitration was separated a a second fraction by vacuum distillation and was nitrate again. This second nitration required the use of 70% or mor concentrated nitric acid in the mixture with 98% sulfuri acid. The reaction was exothermic and required cooling witl an ice-water bath, during the time of addition of the nitratio mixture. This was followed by heating to complete th conversion of the 2-nitro-4-tertbutylanisole to the desire 2,6-dinitro-4-terbutylanisole. Similarly to the first nitration, also in this reation, a by-product, 2,4-dinitroanisole was formed, with the ratio of 10:1. A small amount (below 2%) of the starting material was also present in the post reaction mixture even after extended (up to 25 hours) reaction time. This nitration must be carried on in a solvent such as ethylene dichloride because it is very difficult to avoid the formation of the 2,4,6-trinitroanisole if the reaction is done without any solvent.

EXAMPLE 5

Nitration of the 2-nitro-4-tertbutylanisole

A solution of 4.18 g (20 mmols) of 2-nitro-4-tertbutylanisole in 20 ml of ethylene dichloride was placed in a 50 ml two necked round-bottomed flask equipped with a thermometer, dropping funnel and a magnetic stirring bar. Next the flask was placed in an ice-water bath and the contents were stirred and cooled. When the temperature reaches +4° C. a mixture of 1.89 g (2 ml, 30 mmoles) of 70% nitric acid with 5.88 g (3 ml, 60 mmoles) of 98% sulfuric acid was dropped at such a rate, to keep the reaction mixture temperature below +10° C. Following addition, the cooling bath was removed and the temperature of the reaction mixture was increased to 50° C. and maintained so for the next 2.5 hours. After this time the composition of the mixture was determined by NMR to be 89.2 mol % of 2,6-dinitro-4-tert-butylanisole, 2.5 mol % of the 2-nitro-4-tertbutylanisole and 8.3 mol % of the 2,4-dinitroanisole.

EXAMPLE 6

Separation of the 2,6-dinitro-4-tertbutylanisole from Post-nitration mixture After completing the second nitration, stirring and heating of the reaction mixture was stopped. The mixture separated into two layers: a lower layer consisting of waste acids and an upper organic layer that was collected and without additional purification subjected to evaporation of ethylene dichloride in a rotary evaporator under 20 mmHg at 40° C. This afforded a crystalline mass with mp above 75° C. that was then subjected to hydrolysis. The crystals were diluted with 5 ml of water and the pH of the water layer was adjusted to 7.5 by addition of the required amount of 10% sodium hydroxide followed by addition of 80 mg (2 mmols) of solid sodium hydroxide. The resulting mixture was boiled for an hour and then cooled and extracted with two 10 ml portions of ethylene dichloride. Next, the extract was concentrated by means of rotary evaporation at 40° C. temperature and 20 mmHg pressure to yield an oily product that crystallized after standing. That product was then recrystallized from 5 ml of methanol to yield 4.08 g (79.2% yield) of 99.4% pure 2,6-dinitro-4-tertbutylanisole (the only impurity present was 2-nitro-4-tertbutylanisole). The water layer from the product separation was acidified by addition of 1 ml of 6N hydrochloric acid and the precipitated 2,4-dinitrophenol was extracted with two 5 ml portions of ethylene dichloride. This solution was rotary evaporated at 40° C. temperature and 20 mmHg pressure to yield a mixture of 305 mg (98.4%) of 2,4-dinitrophenol and 5 mg of 2,6-dinitro-4-tertbutylphenol.

The one step dinitration of 4-tertbutylanisole

The nitration procedure in this case was not much different than in the two step process just described. It was done however, without intermediate separation of the 4-nitroanisole that is subjected to second nitration to yield 2,4-dinitroanisole. Additional quantities of the 2,4-dinitroanisole were formed from detertbutylation/nitration of the 2-nitro-4-tertbutylanisole, but in this case the formation of the two isomeric sigma-complexes was very much in favor of the desired one, which after departure of a proton yielded 2,6-dinitro-4-tertbutylanisole in the ratio ~9:1 with 2,4-dinitroanisole. Also in this case the time necessary to complete full conversion of the 2-nitro-4-tertbutylanisole was relatively long. Because of that, more concentrated −98% nitric acid and 5% oleum are better used for the second nitration.

EXAMPLE 7

A solution of 16.4 g (0.1 mole) of 4-tertbutylanisole in 35 ml of ethylenedichloride was placed in a 50 ml two necked round bottomed flask equipped with a thermometer and a dropping funnel with pressure equilibration and placed in an ice-water bath. Into this solution, with good stirring a 5 ml (7.5 g, 1.2 mole) of pure 98% nitric acid was added at such a rate to maintain the temperature below 5° C. It took 25 minutes to complete the addition and an additional 45 minutes of stirring at 20° C. to complete the reaction. After this time, the temperature of the reaction mixture was decreased to 0° C. by applying ice-water bath and a mixture of 7.5 ml of 98% nitric acid with 10 ml of 98% sulfuric acid and 5 ml of 15% oleum was dropped while maintaining strong stirring into the reaction mixture at such a rate as to maintain the temperature of the reaction mixture below 5°. It took 35 minutes to complete this addition. At this time the concentration of the components of the mixture were determined by NMR to be: 45.15 mol % of the 2,6-dinitro-4-tertbutylanisole, 21.55 mol % of the 2-nitro-4-tertbutylanisole, 3.17 mol % of the 4-nitroanisole and 30.13 mol % of the 2,4-dinitroanisole. To nitrate the rest of the intermediates the temperature of the reaction mixture was increased to 40° C. within two hours and maintained so for the next three hours. At this point the composition of the mixture was determined by NMR to be: 34 mol % of the 2,4-dinitroanisole, 64 mol % of the 2,6-dinitro-4-tertbutylanisole and 2 mol % of the 2-nitro-4-tertbutylanisole. Next, the stirring and heating of the mixture was stopped and the lower layer waste acids were separated from the upper organic layer. The acids mixture was then washed with an additional portion of 15 ml of ethylene dichloride and the solution was combined with the organic layer. The combined solutions were then concentrated by means of rotary evaporation at 40° C. under 20 mmHg yielding a light yellow crystalline product with mp above 75° C.

This product was then subjected to hydrolytic separation of the 2,4-dinitrophenol in accordance with the procedure described in Example 6 to afford 6.18 g (98.9% yield) that corresponds to 33.6% of total yield of the 2,4-dinitrophenol separated and 19.37 g 2,6-dinitro-4-tertbutylanisole (95.2% yield, calculated on the theoretical yield possible) contaminated with 3.88 g of the 2-nitro-4-tertbutylanisole. Subsequent crystallization from methyl alcohol (20 ml, cooled −5° C.) afforded 14.72 g of 99.4% pure 2,6-dinitro-4-tertbutylanisole with 57.5% total yield.

The crystallization of the same purity material from 60 ml of 60% aqueous acetic acid afforded 99.6% pure material with 56.7% total yield.

EXAMPLE 8

The first nitration step was performed in the same manner as in the Example 7 but in the second nitration step we used 11.7 ml of 98% nitric acid and 20 ml of 7.5% oleum. This translates to a 100% excess of the nitric acid in comparison with the 50% excess used in the Example 7. The time of addition and the other parameters of the reaction and product separation were also identical. As a result a cleaner 2,6-dinitro-4-tertbutylanisole containing only 1.1% of the 2-nitro-4-tertbutylanisole was obtained (crude product without crystallization) but with a slightly lower (55.2%) total yield. In this case the yield of the 2,4-dinitrophenol was 6.74 g. That corresponds to 36.6% of total yield.

In summary, numerous benefits have been described which result from employing the concepts of the present invention. A more environmentally sound and economical process for the production of N-alkyl-dinitroalkylaniline has been described. In this description, reference has been made to certain preferred steps in the process. However, as obvious modifications or variations thereof will become apparent to those skilled in the art, the invention is not to be considered as limited thereto.

We claim:

1. A process for producing N-sec-butyl-4-tert-butyl-2,6-dinitroaniline, comprising:

reacting 4-tert-butylphenol with a halide free methylating agent to produce 4-tert-butylanisole;

reacting 4-tert-butylanisole with nitric acid to produce 2-nitro-4-tertbutylanisole;

reacting 2-nitro-4-tertbutylanisole with an acid mixture of nitric acid and sulfuric acid to produce 2,6-dinitro-4-tertbutylanisole; and reacting 2,6-dinitro-4-tertbutylanisole with sec-butylamine to produce N-sec-butyl-4-tert-butyl-2,6-dinitroaniline.

2. The process set forth in claim 1, including separating 2-nitro-4-tertbutylanisole from a 4-nitroanisole byproduct by vacuum distillation.

3. The process set forth in claim 1, including separating 2,6-dinitro-4-tertbutylanisole from a 2,4-dinitroanisole by-product by hydrolytic separation.

4. The process set forth in claim 1, wherein said halide free methylating agent is dimethyl sulfate.

5. A process for producing N-sec-butyl-4-tert-butyl-2,6-dinitroaniline, comprising:

reacting 4-tert-butylphenol with a halide free methylating agent to produce 4-tert-butylanisole;

reacting 4-tert-butylanisole with nitric acid to produce 2-nitro-4-tertbutylanisole;

reacting 2-nitro-4-tertbutylanisole with an acid mixture of nitric acid, sulfuric acid and oleum to produce 2,6-dinitro-4-tertbutylanisole; and reacting 2,6-dinitro-4-tertbutylanisole with sec-butylamine to produce N-sec-butyl-4-tert-butyl-2,6-dinitroaniline.

6. The process set forth in claim 5, including separating 2,6-dinitro-4-tertbutylanisole from a 2,4-dinitroanisole by-product by hydrolytic separation.

7. The process set forth in claim 5, wherein said halide free methylating agent is dimethyl sulfate.

8. A process for producing N-sec-butyl-4-tert-butyl-2,6-dinitroaniline, comprising:

reacting 4-tert-butylanisole with nitric acid to produce 2-nitro-4-tertbutylanisole;

reacting 2-nitro-4-tertbutylanisole with an acid mixture of nitric acid, sulfuric acid and oleum to produce 2,6-dinitro-4-tertbutylanisole; and reacting 2,6-dinitro-4-tertbutylanisole with sec-butylamine to produce N-sec-butyl-4-tert-butyl-2,6-dinitroaniline.

9. A process for producing N-sec-butyl-4-tert-butyl-2,6-dinitroaniline, comprising:

reacting 4-tert-butylanisole with nitric acid to produce 2-nitro-4-tertbutylanisole;

reacting 2-nitro-4-tertbutylanisole with an acid mixture of nitric acid, sulfuric acid and oleum to produce 2,6-dinitro-4-tertbutylanisole; and reacting 2,6-dinitro-4-tertbutylanisole with sec-butylamine to produce N-sec-butyl-4-tert-butyl-2,6-dinitroaniline.

10. A process for producing N-sec-butyl-4-tert-butyl-2,6-dinitroaniline, comprising:

reacting 4-tert-butylphenol with a halide free methylating agent to produce a first reaction intermediate;

reacting said first reaction intermediate with nitric acid to produce a mononitro-substituted reaction intermediate;

reacting said mononitro-substituted reaction intermediate with an acid mixture selected from a group consisting of nitric acid and sulfuric acid or nitric acid, sulfuric acid and oleum to produce a dinitro-substituted reaction intermediate;

reacting said dinitro-substituted reaction intermediate with an amine selected from a group including sec butylamine and 1-ethylpropylamine to produce N-alkyl-dinitroalkylaniline.

11. The process set forth in claim 10, wherein said reacting of alkylphenol with methylating agent includes:

(a) preparing an aqueous suspension of alkylphenol;

(b) adding a metal hydroxide and a dialkyl sulfate or mixture thereof into said aqueous suspension; and (c) collecting the first reaction intermediate as an upper layer of a resulting two layer system.

* * * * *